United States Patent
Zeng et al.

(10) Patent No.: US 9,024,013 B2
(45) Date of Patent: May 5, 2015

(54) METHOD FOR PURIFYING ROCURONIUM BROMIDE

(75) Inventors: Zhiwen Zeng, Zhejiang (CN); Peng Wang, Zhejiang (CN); Wenling Zhang, Zhejiang (CN); Xini Zhang, Zhejiang (CN)

(73) Assignee: Zhejiang Huahai Pharmaceutical Co., Ltd, Zhejiang (CN)

( * ) Notice: Subject to any disclaimer, the term of this patent is extended or adjusted under 35 U.S.C. 154(b) by 0 days.

(21) Appl. No.: 14/122,679

(22) PCT Filed: Apr. 25, 2011

(86) PCT No.: PCT/CN2011/073256
§ 371 (c)(1),
(2), (4) Date: Nov. 27, 2013

(87) PCT Pub. No.: WO2012/145888
PCT Pub. Date: Nov. 1, 2012

(65) Prior Publication Data
US 2014/0200340 A1  Jul. 17, 2014

(51) Int. Cl.
*C07J 43/00* (2006.01)

(52) U.S. Cl.
CPC .............. *C07J 43/003* (2013.01); *C07J 43/00* (2013.01)

(58) Field of Classification Search
CPC ..................................... C07J 43/003
USPC ............................................ 540/96
See application file for complete search history.

(56) References Cited

U.S. PATENT DOCUMENTS

2006/0058275 A1  3/2006  Friedman et al.

FOREIGN PATENT DOCUMENTS

| | | |
|---|---|---|
| CN | 101397329 A | 4/2009 |
| CN | 101653412 A | 2/2010 |
| CN | 101993470 A | 3/2011 |
| EP | 0287150 A1 | 10/1988 |
| GB | 2445746 A | 7/2008 |
| WO | 2007033348 A2 | 3/2007 |
| WO | 2008087383 A1 | 7/2008 |

OTHER PUBLICATIONS

International Search Report for PCT/ CN2011/073256, Feb. 9, 2012.
Written Opinion for PCT/ CN2011/073256, Jan. 19, 2012.
Search Report regarding a European counterpart application 11864391.5, issued Sep. 5, 2014, 4 pages.

*Primary Examiner* — Brenda Coleman
(74) *Attorney, Agent, or Firm* — Kilpatrick Townsend & Stockton LLP

(57) ABSTRACT

Provided is a method for purifying rocuronium bromide, which comprises: formulating crude rocuronium bromide to be purified into an aqueous solution, distilling off excess residue solvents at reduced pressure, absorbing by adding active carbon or silica gel, then filtrating, quick freezing the filtrate into ice, and then lyophilizing to obtain rocuronium bromide.

10 Claims, 1 Drawing Sheet

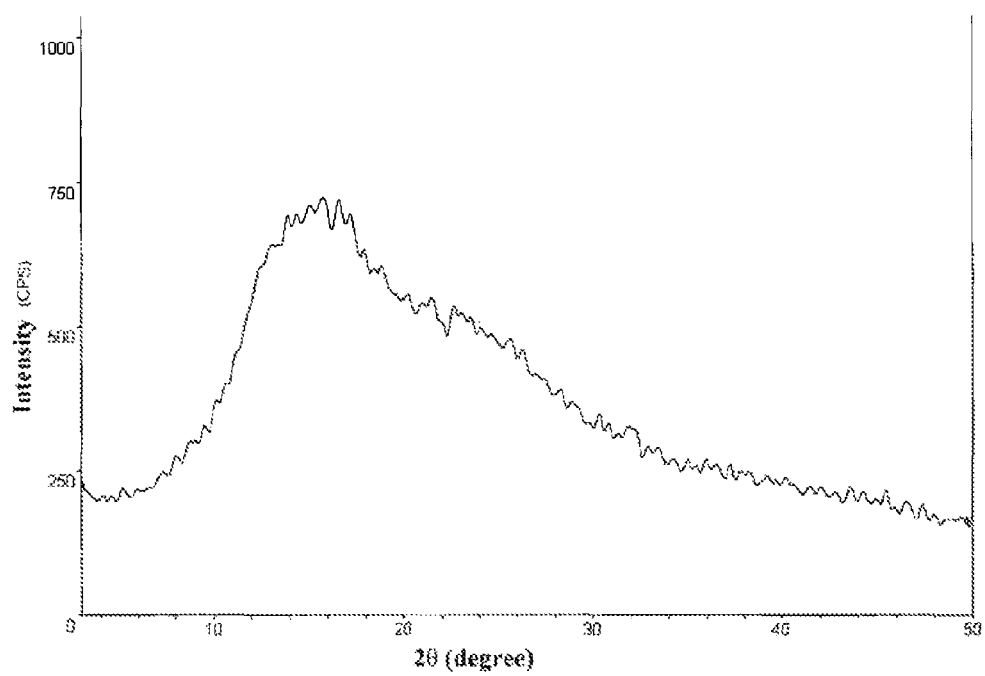

METHOD FOR PURIFYING ROCURONIUM BROMIDE

FIELD OF THE INVENTION

The present invention relates to the field of medicine, particularly to a method for purifying the drug rocuronium bromide.

BACKGROUND OF THE INVENTION

Rocuronium bromide is a steroidal non-depolarizing muscle relaxant developed by a Dutch company Organon, and was firstly marketed in the US in 1994. This drug is currently the most widely used muscle relaxant internationally, and in North America and most European countries, the consumption thereof is the highest among all the muscle relaxants. Rocuronium bromide is a novel mono-quaternary ammonium muscle relaxant, and is used as an anaesthetic adjuvant for endotracheal intubation under anesthesia and muscle relaxation during surgery, and is the non-depolarizing muscle relaxant having the shortest onset time in clinical use. It is characterized in the quick onset of action, rapid recovery, week inhibition to the cardiovascular system, and having no effect of histamine release. Rocuronium bromide has the following chemical structural formula:

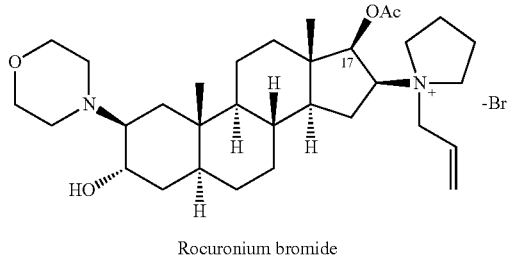

Rocuronium bromide

European patent EP0287150 firstly discloses a process for preparing rocuronium bromide, wherein rocuronium bromide is obtained by subjecting 2β-(4-morpholinyl)-16β-(1-pyrrolidinyl)-5α-androstan-3α-ol, 17β-acetate (hereafter referred to as Rocu 8) and 3-bromopropylene to a quaternization reaction, and the reaction equation thereof is as follows:

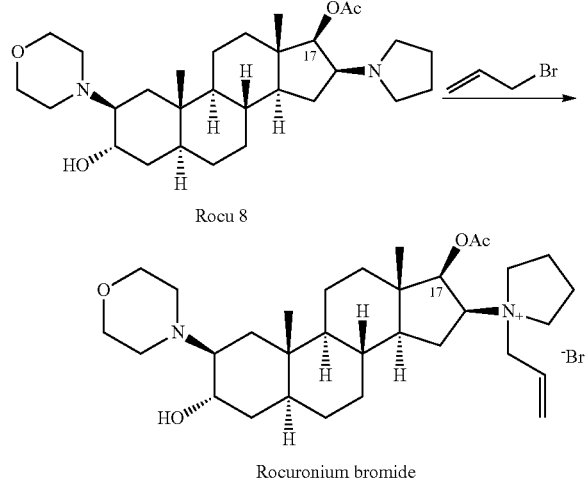

After completion of the reaction, the reaction liquid is evaporated to dryness, the product is dissolved in dichloromethane, and the resultant solution is added to diethyl ether to collect and obtain rocuronium bromide. The rocuronium bromide obtained from this method has very high content of residual solvent, and it is found by experiments that the content of residual solvent can be up to 16%, and the residual 3-bromopropylene is up to approximately 400 ppm.

In addition, the ester group in 17-position of the structure of rocuronium bromide will be hydrolyzed to form a hydrolyzed impurity (impurity C in USP pharmacopeia), which is formed by reaction of the incompletely reacted material of the reactant Rocu 8 in the previous step with 3-bromopropylene, and the simultaneous hydrolysis reaction occurring during post-processing of rocuronium bromide or with the water contained in itself. It is the main impurity which needs to be controlled in formulation product, and has the following chemical structural formula:

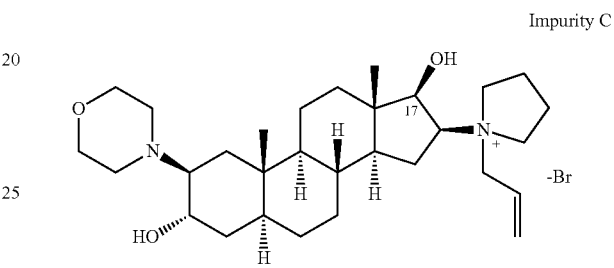

Impurity C

Furthermore, the impurity generated by decomposition of the incompletely reacted Rocu 8 and decomposition of rocuronium bromide during post-processing and storage (impurity A in USP pharmacopeia) is also the main impurity which needs to be controlled in formulation product, and has the following chemical structural formula:

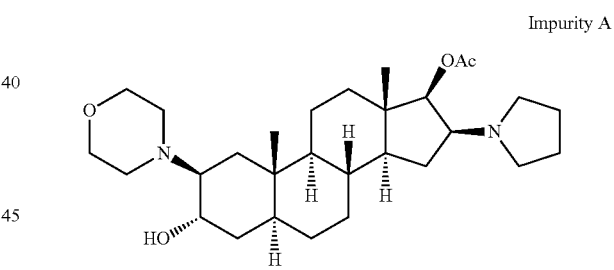

Impurity A

Moreover, it is reported that lower halohydrocarbons have genotoxicity, and generally the toxicity decreases in the order of bromohydrocarbons, chlorohydrocarbons, and fluorohydrocarbons. Consequently, the raw material 3-bromopropylene used in synthesis of rocuronium bromide is also a potential substance having genotoxicity.

US patent US2006058275 discloses a method for lyophilizing rocuronium bromide, wherein a buffer solution comprising acetic acid and sodium acetate is added during the lyophilization. Since water and acetic acid in the buffer system tend to decrease as the lyophilization goes on, the PH value during lyophilization is unstable, the final product is severely decomposed, and the resultant product is not a single, pure rocuronium bromide. British patent GB2445746 mentions a process for lyophilizing a aqueous solution of rocuronium bromide: rocuronium bromide is dissolved in an aqueous solution with a PH of lower than 4~5 (adjusting the PH value with carbon dioxide), then carbon dioxide is employed to adjust the PH to 8 or lower, the solution is then concentrated and detected for the amount of residual solvents, and then lyophilization is carried out. This process is tedious in operation, and the amount of residual 3-bromopropylene in the resultant product is more than 100 ppm. Therefore, it is of great significance to develop a method for preparing rocuronium bromide with high purity.

SUMMARY OF THE INVENTION

The object of the present invention is to provide a method for preparing rocuronium bromide with high purity.

Rocuronium bromide is a water soluble drug which is extremely susceptible to hydrolysis and unstable. Unknown impurities is easily generated when heated, and solvates with many solvents are easily formed, such that the residual solvents are very difficult to remove. Since the bonded organic solvents is dissociate after rocuronium bromide is dissolved in water, the solvent is easy to remove at this time, and rocuronium bromide is relatively stable under low temperature. In view of this, it is very suitable to purify this product by using lyophilization. However, in a normal lyophilization process, the resicual solvents in the product still cannot be controlled well.

Upon investigation, the present inventors have found the following aspects.

Firstly, rocuronium bromide is formulated with water into 5~40 mass % aqueous solution, with a PH value of between 8~9.5, and the higher the concentration of rocuronium bromide is, the lower the PH value of the solution is. The rocuronium bromide aqueous solution hydrolyzes more slowly under low temperature, at a PH value of 8~9.5, and under good protection of nitrogen gas.

Secondly, using active carbon or silica gel to remove impurities, especially to absorb 3-bromopropylene, in rocuronium bromide is very effective. Upon investigation, the present inventors have found that, by employing the same technology, without addition of active carbon or silica gel, the amount of residual 3-bromopropylene in the resultant rocuronium bromide is more than 100 ppm, while after addition of active carbon or silica gel, the amount can be controlled to 10 ppm or less.

More delightfully, the present inventors have found that, after being treated with the method of the present invention, the resultant product is also much more stable compared to the untreated product. Upon investigation, the present inventors have found that, when the moisture in rocuronium bromide is 4% or more, a storage period of about 10 days at room temperature renders the hydrolyzed impurities being out of limits and causes a large amount of unknown impurities to appear; after being purified with the method of the present invention, and the moisture is controlled to be 4% or less and preferably 0.5% or less, the level of impurities is substantially unchanged after a storage period of one month at room temperature.

The present invention provides a method for purifying crude rocuronium bromide, which employs the following protocol:

formulating crude rocuronium bromide to be purified into a 5~40 mass % aqueous solution, distilling under reduced pressure of 20±5 mbar, adding active carbon or silica gel in an amount of 1~5% by mass of the crude rocuronium bromide for adsorption, filtering, and quickly freezing the filtrate into ice, which is then subjected to lyophilization to obtain rocuronium bromide.

Preferably, the aqueous solution contains 15~35% rocuronium bromide by mass.

More preferably, the distillation under reduced pressure is carried out under the protection of nitrogen gas.

More preferably, the distillation under reduced pressure is carried out at a temperature of 0~15° C., and the distillation time is no more than 5 hours, preferably 2~5 hours.

Preferably, the temperature for quickly freezing the material into ice is −80~−20° C., preferably −40~−20° C.

Preferably, the material temperature for the primary drying at the beginning of the lyophilization is −80~−10° C., preferably −40~−10° C.

Preferably, the primary drying is carried out for 0~30 hours, more preferably within 15 hours.

Preferably, the temperature for the desorption drying in the lyophilization is 15~40° C., preferably 25~40° C.

Preferably, the desorption drying is carried out for 0~20 hours, preferably 3~15 hours.

In comparison with the prior art, the purification method of the present invention can effectively control the amount of residual 3-bromopropylene and the increase of hydrolyzed impurity C, and enables both the contents of water and residual solvents to conform to the USP33 standard stipulated in US pharmacopeia. The technique of the method of the present invention is simple in technology, convenient in operation, and easy to control, and the product obtained therefrom has good quality. The HPLC purity of the obtained rocuronium bromide can achieve up to 99% or more, the HPLC area of impurity C is less than 0.20%, the amount of residual 3-bromopropylene is less than 10 ppm, the moisture is less than 4.0%, and the residual solvents conform to the requirements of the pharmacopeia. The method of the present invention achieves the improvement and optimization of the prior art, is very beneficial to industrial production, and is very competitive in the market.

DESCRIPTION OF THE DRAWINGS

FIG. 1 is an X-ray diffraction spectrum of the lyophilized powder of rocuronium bromide.

DETAILED EMBODIMENTS

To further understanding of the present invention, the preferred embodiments of the present invention are described in combination with examples. However, it is to be understood that these descriptions are only for the further illustration of the characteristics and advantages of the present invention, rather than to limit the claims of the present invention.

The method for purifying rocuronium bromide provided in the present invention is specifically carried out as follows.

Step 1: formulating the crude rocuronium bromide to be purified into a 5~40 mass % aqueous solution, distilling under reduced pressure of 20±15 mbar, adding active carbon or silica gel in an amount of 1~5% by mass of the crude rocuronium bromide for adsorption.

Wherein, the mass concentration of the rocuronium bromide aqueous solution is preferably 15~35%. The distillation under reduced pressure is carried out at a temperature of 0~15° C., preferably 0~10° C. The distillation time is 0~5 hours, preferably 2~5 hours.

Preferably, the distillation under reduced pressure is carried out under the protection of nitrogen gas.

Step 2: filtering the aqueous solution of rocuronium bromide, and lyophilizing the filtrate.

The aqueous solution treated by active carbon or silica gel is filtrated, and the filtrate is put into lyophilization trays of the lyophilizer. To assure the lyophilization effect, the thickness of the liquid material should not be too thick.

Step 3: quickly freezing the filtrate, and then starting lyophilization.

Wherein, the material is quickly freezed to a temperature of −80~−2.0° C., preferably −40~−30° C. The temperature for the primary drying in the lyophilization is set to −40~−10° C., preferably −25~−10° C. The time of duration for the primary drying is 0~30 hours, more preferably 15 hours or less. The temperature for the desorption drying is set to 15~40° C., preferably 25~40° C. The time of duration for the desorption drying is 0~20 hours, more preferably 3~15 hours. The X-ray diffraction spectrum of the obtained crystalline powder of rocuronium bromide is shown in FIG. 1, from which it can be seen that the obtained powder is amorphous.

The purification method of the present invention can effectively control the amount of residual 3-bromopropylene and the increase of hydrolyzed impurity C, and enables both the contents of water and residual solvents to conform to the USP33 standard stipulated in US pharmacopeia. The technique of the method of the present invention is simple in technology, convenient in operation, and easy to control, and the product obtained therefrom has good quality. The HPLC purity of the obtained rocuronium bromide can achieve up to 99% or more, the HPLC area of impurity C is less than 0.20%, the amount of residual 3-bromopropylene is less than 10 ppm, the moisture is less than 4.0%, and the total amount of residual solvents conform to the requirements of the pharmacopeia.

The effects of the present invention will be illustrated by specific examples. However, the protection scope of the present invention is not limited by the following examples.

Example 1

Purifying the Crude Rocuronium Bromide with the Method of the Present Invention

A crude rocuronium bromide was prepared with reference to the method in EP0287150. Upon detection, the residual solvents in the crude product were: 3-bromopropylene 379 ppm, dichloromethane 3000 ppm, and diethyl ether 15%. HPLC purity of impurity A is 0.08%, and no impurity C was detected.

10.0 g the above crude rocuronium bromide was dissolved in 30.0 g of deionized water, and the solution was cooled to 5° C. Displacement with nitrogen gas and then distillation under reduced pressure were carried out. The distillation pressure was controlled to be about 20±5 mbar (positive pressure). After treatment for 3.5 hours, 0.4 g silica gel was added, and the mixture was kept at the temperature under stirring for 30 min. The mixture was filtered, and the filtrate was collected in a tray and then quickly freezed into ice at −40° C. The vacuum degree was controlled to 0~5 Pa to carry out lyophilization. Finally, the mixture was warmed up to 35° C. and vacuum drying was carried out at the temperature for 10 hours, to yield 8.2 rocuronium bromide.

After lyophilization, the residual solvents in the rocuronium bromide were 3-bromopropylene: 6.0 ppm, diethyl ether: 200 ppm. The moisture was 0.50%, the HPLC area of impurity A was 0.02%, and the HPLC area of impurity C was 0.09%.

Example 2

Comparison of the Method of the Present Invention with a Conventional Purifying Method Preparation of crude rocuronium bromide: 200.0 g 2β-(4-morpholinyl)-16β-(1-pyrrolidinyl)-5α-androstan-3α-ol, 17β-acetate and 140 ml 3-bromopropylene were added in a 1000 mL bottle under the protection of nitrogen gas at a constant temperature of 25° C. under mechanical stirring. The reaction was completed after 1.25 hours. 500 ml acetonitrile was added under stirring for dissolution. The solution was filtered by suction, and the filtrate was concentrated by rotary evaporation to dry. 800 ml dichloromethane was added for dissolution and the solution was slowly added dropwise into 48 L methyl tert-butyl ether under vigorous stirring. After completion of the addition, the mixture was stirred in an ice bath for 1 hour. The mixture was filtered, and the filter cake collected was subjected to vacuum drying at room temperature for 2 days to yield 260.5 g crude rocuronium bromide.

The above crude rocuronium bromide was detected for residual solvents: 3-bromopropylene was 550 ppm, methyl tert-butyl ether was 9.0%, acetonitrile was 2000 ppm, and dichloromethane was 0.5%. The HPLC area of rocuronium bromide was more than 99.5%, the HPLC area of impurity A was 0.02%, and no impurity C was detected.

The crude rocuronium bromide was subjected to three purification methods which are described in detail as follows.

Method 1. Conventional Vacuum Drying 10.0 g the above crude rocuronium bromide was ground into fine powders, and subjected to vacuum drying in a vacuum drying oven at 40° C. for one day, to yield 8.8 g of rocuronium bromide.

The rocuronium bromide obtained from the vacuum drying was tested, and the results of residual solvents were as follows: 3-bromopropylene was 60 ppm, methyl tert-butyl ether was 400 ppm, acetonitrile was 150 ppm, dichloromethane was 60 ppm; moisture was 3.50%; the HPLC area of impurity C was 0.11%, the HPLC area of impurity A was 0.26%, and two unknown impurities appeared respectively at 1.1 and 1.3 times of the main peak time, the HPLC area of each of them was 0.05%.

Method 2. Purifying the Crude Rocuronium Bromide by the Method of the Present Invention Without Adding Active Carbon And Silica Gel 10.0 g the above crude rocuronium bromide was dissolved in 50.0 g deionized water, and the solution was cooled to 10° C. Displacement with nitrogen gas and then distillation under reduced pressure were carried out. The distillation pressure was controlled to be about 20±5 mbar (positive pressure). After treatment for 3.5 hours, the liquid material was collected in a tray and then quickly freezed into ice at −40° C. The vacuum degree was controlled to 0~5 Pa to carry out lyophilization. Finally, the mixture was warmed up to 35° C. and vacuum drying was carried out at the temperature for 3 hours, to yield 8.9 g rocuronium bromide.

After lyophilization, the residual solvents in the rocuronium bromide were 3-bromopropylene: 17.9 ppm, methyl tert-butyl ether: N.D, acetonitrile: 78 ppm, moisture 2.60%; the HPLC area of impurity A was 0.10%, and the HPLC area of impurity C was 0.30%.

Method 3. Purifying the Crude Rocuronium Bromide by the Method of the Present Invention 10.0 g the above crude rocuronium bromide was dissolved in 50.0 g of deionized water, and the solution was cooled to 10° C. Displacement with nitrogen gas and then distillation under reduced pressure were carried out. The distillation pressure was controlled to be about 20±5 mbar (positive pressure). After treatment for 3.5 hours, 0.4 g active carbon was added, and the mixture was kept at the temperature under stirring for 30 min. The mixture was filtered, and the filtrate was collected in a tray and then quickly freezed into ice at −40° C. The vacuum degree was controlled to be 0~5 Pa to carry out lyophilization. Finally, the mixture was warmed up to 35° C. and vacuum drying was carried out at the temperature for 6 hours, to yield 8.7 g of rocuronium bromide.

After lyophilization, the residual solvents in the rocuronium bromide were 3-bromopropylene: 3.0 ppm, methyl tert-butyl ether: N.D, acetonitrile: 78 ppm. The moisture was 2.6%, the HPLC area of impurity A was 0.02%, and the HPLC area of impurity C was 0.10%.

Table 1 shows the details.

TABLE 1

Comparison of the method of the present invention for purifying crude rocuronium bromide with a conventional method

|  | 3-Bromo propylene | Methyl tert-butyl ether | Acetonitrile | Moisture | Impurity A | Impurity C | Unknown impurities |
|---|---|---|---|---|---|---|---|
| Method 1 | 60 ppm | 400 ppm | 150 ppm | 3.5% | 0.26% | 0.11% | 2, 0.05% |
| Method 2 | 17.9 ppm | N.D | 78 ppm | 2.6% | 0.10% | 0.30% | N.D |
| Method 3 | 3.0 ppm | N.D | 78 ppm | 1.7% | 0.02% | 0.10% | N.D |

Example 3

Moisture and Stability Test of the Crude Rocuronium Bromide

With respect to the stability of rocuronium bromide itself, the lower the residual moisture is, the more stable the product is. Upon investigation, the present inventors found that when the moisture in rocuronium bromide was 4% or more, a storage period of about 10 days at room temperature renders the hydrolyzed impurities being out of limits as stipulated in the USP33 standard and causes a large amount of unknown impurities to appear (see the data as shown in Table 2); when the moisture was controlled to about 0.5%, the levels of impurities were substantially unchanged after a storage period of one month at room temperature.

TABLE 2

Storage stability at room temperature of rocuronium bromide sample with a moisture of 4.5%

| | Substances involved (HPLC) | | | |
|---|---|---|---|---|
| | Impurity A | Impurity C | Single unknown impurity | Total impurities |
| Day 0 | 0.02% | 0.06% | N.D | 0.08% |
| Day 10 | 0.25% | 0.36% | 0.12% | 0.73% |
| Day 20 | 0.30% | 0.40% | 0.20% | 0.90% |
| Day 30 | 0.35% | 0.50% | 0.20% | 1.05% |

TABLE 3

Storage stability at room temperature of rocuronium bromide sample with a moisture of 0.5%

| | Substances involved (HPLC) | | | |
|---|---|---|---|---|
| | Impurity A | Impurity C | Single unknown impurity | Total impurities |
| Day 0 | 0.02% | 0.06% | N.D | 0.08% |
| Day 10 | 0.02% | 0.06% | N.D | 0.08% |
| Day 20 | 0.03% | 0.06% | N.D | 0.09% |
| Day 30 | 0.03% | 0.06% | N.D | 0.09% |

Although the method for purifying rocuronium bromide provided in the present invention has been described by examples, it is apparent that a person skilled in the art can make modifications or proper alterations and combinations to the method for purifying rocuronium bromide described herein to achieve the technique of the present invention without departing from the contents, spirit and scope of the present invention. It should be particularly noted that, all the similar replacements and modifications are obvious to a person skilled in the art and are to be construed to be within the spirit, scope and contents of the present invention.

The invention claimed is:

1. A method for purifying crude rocuronium bromide, characterized in
formulating the crude rocuronium bromide to be purified into a 5~40 mass % aqueous solution, distilling under reduced pressure, adding active carbon or silica gel in an amount of 1~5% by mass of the crude rocuronium bromide for adsorption, filtering, and quickly freezing the filtrate into ice, which is then subjected to lyophilization to obtain rocuronium bromide.

2. The method according to claim 1, characterized in that the aqueous solution contains 15~35% rocuronium bromide by mass.

3. The method according to claim 1, characterized in that, the distillation under reduced pressure is carried out under the protection of nitrogen gas.

4. The method according to claim 1, characterized in that the distillation under reduced pressure is carried out at a temperature of 0~15° C.

5. The method according to claim 1, characterized in that the distillation under reduced pressure is carried out for no more than 5 hours.

6. The method according to claim 5, characterized in that the distillation under reduced pressure is carried out for 2~5 hours.

7. The method according to claim 1, characterized in that the quick freezing into ice is carried out at a material temperature of −80~20° C.

8. The method according to claim 7, characterized in that the quick freezing into ice is carried out at a material temperature of −40~20° C.

9. The method according to claim 1, characterized in that, at the beginning of the lyophilization, the material temperature for the primary drying is −80~10° C.

10. The method according to claim 9, characterized in that, at the beginning of the lyophilization, the material temperature for the primary drying is −40~10° C.

* * * * *